United States Patent
Krill et al.

(10) Patent No.: US 11,661,392 B2
(45) Date of Patent: May 30, 2023

(54) SAFE METHOD FOR TANDEM C-4 OXIDATION TO METHACRYLIC ACID

(71) Applicant: Röhm GmbH, Darmstadt (DE)

(72) Inventors: Steffen Krill, Muehltal (DE); Jalyn Deng, Darmstadt (DE); Markus Maier, Heppenheim (DE)

(73) Assignee: Röhm GmbH, Darmstadt (DE)

( * ) Notice: Subject to any disclaimer, the term of this patent is extended or adjusted under 35 U.S.C. 154(b) by 0 days.

(21) Appl. No.: 17/907,721

(22) PCT Filed: Mar. 25, 2021

(86) PCT No.: PCT/EP2021/057744
§ 371 (c)(1),
(2) Date: Sep. 29, 2022

(87) PCT Pub. No.: WO2021/198014
PCT Pub. Date: Oct. 7, 2021

(65) Prior Publication Data
US 2023/0124059 A1    Apr. 20, 2023

(30) Foreign Application Priority Data
Apr. 3, 2020 (EP) .................................... 20167864

(51) Int. Cl.
*C07C 51/25* (2006.01)

(52) U.S. Cl.
CPC .................................. *C07C 51/252* (2013.01)

(58) Field of Classification Search
CPC ....... C07C 45/35; C07C 51/252; C07C 57/04; C07C 47/22
See application file for complete search history.

(56) References Cited

U.S. PATENT DOCUMENTS

| | | | |
|---|---|---|---|
| 694,362 A | 3/1902 | Fortier et al. | |
| 3,147,084 A | 9/1964 | Franzen et al. | |
| 3,876,693 A | 4/1975 | Erpenbach et al. | |
| 4,031,135 A | 6/1977 | Engelbach et al. | |
| 4,124,634 A | 11/1978 | Gotoh et al. | |
| 4,147,721 A * | 4/1979 | Leacock | C07C 51/46 562/532 |
| 7,799,946 B2 | 9/2010 | Galloway | |
| 8,350,081 B2 | 1/2013 | Balduf | |
| 8,829,235 B2 | 9/2014 | Balduf | |
| 11,472,762 B2 | 10/2022 | Krill et al. | |
| 2007/0010394 A1 | 1/2007 | Atsushi et al. | |
| 2008/0021239 A1 | 1/2008 | Ogawa et al. | |
| 2010/0130648 A1 | 5/2010 | Balduf | |
| 2010/0144931 A1 | 6/2010 | Balduf | |
| 2014/0187817 A1 | 7/2014 | Balduf et al. | |
| 2022/0204436 A1 | 6/2022 | Krill et al. | |

FOREIGN PATENT DOCUMENTS

| | | |
|---|---|---|
| EP | 0 300 769 | 1/1989 |
| GB | 2041930 | 9/1980 |

OTHER PUBLICATIONS

International Search Report dated May 20, 2021, in PCT/EP2021/057744, 3 pages.
Written Opinion dated May 20, 2021, in PCT/EP2021/057744, 6 pages.
U.S. Pat. No. 8,829,235, Sep. 9, 2014, 2010/0130648, Torsten Balduf.
U.S. Pat. No. 8,350,081, Jan. 8, 2013, 2010/0144931, Torsten Balduf.
U.S. Appl. No. 14/240,547, filed Feb. 24, 2014, 2014/0187817, Balduf et al.
U.S. Pat. No. 11,472,762, Oct. 18, 2022, 2022/0204436, Krill et al.

* cited by examiner

*Primary Examiner* — Yevgeny Valenrod
*Assistant Examiner* — Blaine G Doletski
(74) *Attorney, Agent, or Firm* — Grüneberg and Myers, PLLC

(57) ABSTRACT

An improved process can be used for the production of methacrylates, in particular methacrylic acid and/or methyl methacrylate (MMA). Specific embodiments of this process can be used for the safe and efficient production of these products from C-4-based raw materials, in particular those based on isobutylene or tert-butanol as raw materials. With this novel process, it is possible to operate such processes for a longer period of time without any safety or cleaning related shutdowns. This makes it possible to carry out such processes as simple, economic, and environmentally friendly as possible.

10 Claims, 5 Drawing Sheets

SAFE METHOD FOR TANDEM C-4 OXIDATION TO METHACRYLIC ACID

CROSS-REFERENCE TO RELATED APPLICATIONS

This application is the National Stage entry under § 371 of International Application No. PCT/EP2021/057744, filed on Mar. 25, 2021, and which claims the benefit of priority to European Application No. 20167864.6, filed on Apr. 3, 2020, The content of each of these applications is hereby incorporated by reference in its entirety.

BACKGROUND OF THE INVENTION

Field of the Invention

The present invention relates to an improved process for the production of methacrylates, in particular methacrylic acid and/or methyl methacrylate (MMA). Furthermore, the present invention relates to a process and specific embodiments of this process for the safe and efficient production of these products from C-4-based raw materials, in particular those based on isobutylene or tert-butanol as raw materials.

With this novel process, it is possible to operate such processes for a longer period of time without any safety or cleaning related shutdowns. This makes it possible to carry out such processes as simple, economic and environmentally friendly as possible.

Description of Related Art

There are several methods well known for producing Methyl methacrylate (MMA) in an industrial scale. One of these methods for example is a method whereby MMA is synthesized from hydrocyanic acid and acetone via the resulting acetone cyanohydrin (ACH) as the central intermediate product.

This process has the disadvantage that very large quantities of ammonium sulfate are obtained, the preparation of which is associated with very high costs. Other processes using a raw material base other than ACH have been described in the relevant patent literature and have now been implemented on a production scale. In this context, C4-based raw materials such as isobutylene or tert-butanol are also used today as starting materials, which are converted into the desired MMA respectively methacrylic acid derivatives in several process steps.

Here, in a first step isobutylene or tert-butanol is oxidized to methacrolein, which is then converted with oxygen to obtain methacrylic acid. The methacrylic acid obtained is finally esterified with methanol. Further details on this process are available in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441.pub2 as well as in Krill and Rühling et. al. "Many paths lead to methacrylic acid methyl ester", WILEY-VCH Verlag GmbH & Co. KGaA, Weinheim, doi.org/10.1002/ciuz.201900869.

A distinction has to be made between three processes based on C4 raw materials for producing MMA on this basis. The raw materials used here could differ and are, for example, isobutene itself, which is available as raw material from a cracker, tert-butanol, which is converted to isobutene by water elimination, or, as a third alternative, methyl tert-butyl ether, which is converted to isobutene by methanol elimination. In summary, the following three routes are well known:

Process A, "Tandem C4 Direct Oxidation" process, without any intermediate isolation of methacrolein: Here, methacrolein is produced from isobutene in a first step, which is oxidized to methacrylic acid in step 2, before finally MMA is obtained by esterification of methacrylic acid with methanol in step 3. This process is also referred to in the literature as the "tandem process", since the process gas of the first stage is directly oxidized to methacrylic acid without isolation of the intermediate product methacrolein.

Process B, "Separate C4 Direct Oxidation" process: Here, similar to process A, methacrolein is produced from isobutene in a first step, which is isolated and purified in liquid form in a separate process step, before being evaporated and oxidized to methacrylic acid in step 3 and finally converted by esterification to MMA in a step 4.

Process C, "Direct Metha Process" or Direct Oxidative Esterification Process: Here, too, methacrolein is produced from isobutene in a first step, which is also first isolated and intermediately purified in a step 2, before it is directly oxidatively esterified to MMA in a step 3.

All processes described are well documented in the state of the art, including (i) IHS Chemical Process Economics Program, Review 2015-05, R. J. Chang, Syed Naqvi or (ii) Vapor Phase Catalytic Oxidation of Isobutene to Methacrylic Acid, Stud. Sci. Catal. 1981, 7, 755-767.

Process A and B have in common that methacrylic acid is the main product which can be optionally converted to methyl methacrylate in an esterification reaction with methanol. Usually, a Brönstedt active catalyst is used for this last esterification step. Especially, it is common to use a dissolved strong acid in the homogeneous variant. Preferred acids are sulfuric acid, methane sulfonic acid, or an acidic ion exchanger with corresponding immobilized acidic functions.

Method C, the "Direct Metha Process", proceeds in the first two steps analogously to method B. After gas phase oxidation of isobutene or tert-butyl alcohol, crude methacrolein is processed in liquid form. This is followed by a different step of the so-called direct oxidative esterification of methacrolein with methanol in presence of an oxygen-containing gas, such as air. The reaction is preferably conducted in the presence of a heterogeneous powder-like precious metal contact in liquid phase. Here, MMA is obtained directly and no intermediate step of methacrylic acid production in the gas phase is necessary.

Processes A and B are therefore characterized by the fact that only a partial conversion of the methacrolein contained in the gas mixture takes place when passing through the second oxidation stage. In addition to carbon oxide and carbon dioxide, a large number of other reaction products are formed, namely formaldehyde, acetic acid, acetone, acetaldehyde and acrolein. In the subsequent processing steps, unreacted methacrolein must be isolated from the desired product methacrylic acid. Usually this separation task is carried out by at least one distillation or extraction step. Methacrolein itself is absorbed from the process gas, and is further processed, partially purified, isolated by a desorption process and optionally at least one distillation process. After absorption and desorption, optionally further distillation takes place. The presence of highly volatile but condensable components in addition to acrolein, depending on the separation effort, a crude methacrolein, usually a methacrolein mixture with a methacrolein concentration>70 wt. % is obtained. This means that the crude methacrolein mixture, obtained in liquid form by separation from methacrylic acid, may contain certain amounts of components with similar or lower boiling points relative to methacrolein, besides some trace components like methacrylic acid, acetic acid, terephthalic acid and stabilizers. Some of these secondary components have critical flash points and influence the explosion properties of resulting mixtures with oxygen-containing gases. The process of reintroducing the recycled methacrolein into the main process, for example before the second reaction stage, represents a particularly safety-critical step in the overall process. Numerous suggestions have already been made in the state of the art to solve this problem.

Especially, there are following safety performance difficulties to be optimized:

1) The first reaction step involves the production of a gas mixture containing isobutene, water vapor and oxygen, comprising an isobutene content of 3 to 10 vol %. With regard to its explosion properties, this concentration is above the upper explosion limit, at least for certain isobutene mixtures which contained below 5 vol %. The resulting gas mixture after leaving the first reactor contains 3 to 10 vol % organic components. However, by nature of the reaction oxygen is consumed during the reaction of isobutene to methacrolein, therefore the oxygen content in the resulting process gas of the first stage oxidation is depleted in oxygen to a level that the mixture is not explosive, and the oxygen concentration is well below 8 vol %. Before this process gas can be converted in the second partial oxidation stage, the oxygen content must be increased in order to achieve a stoichiometry from oxygen to methacrolein which is sufficient for the reaction of methacrolein to methacrylic acid but also maintains the catalyst in a sufficiently oxidized state. This is necessary to ensure that the catalyst has an optimal long lifetime which offers economic advantages. It is known in the state of the art that these conditions are fulfilled if the oxygen/methacrolein ratio is 1.5 to 3.5. The rather low ratios are advantageous for the safety of the process, but disadvantageous for the lifetime of the catalyst. The rather higher ratios are advantageous for the lifetime of the catalyst but produce gas mixtures which might be explosive or can be considered explosive if certain levels of fuel are given. These explosive gas mixtures usually have oxygen contents higher than 9 vol %.

2) Based on the catalyst condition, the two temperature-controlled reaction zones have different temperature levels. The gas stream leaving the first reaction zone must be cooled down before entering the second reaction zone. This is the case because in the state of the art processes the salt bath temperature of the first stage, whereby the salt bath temperature is the direct indication for the reaction temperature, is 30° C. to 100° C. higher than the salt bath temperature of the corresponding second stage. Usually the hotter process gas of the first stage is cooled by mixing with a colder oxygen containing gas stream which contains also recycled methacrolein. By this procedure one is able to increase oxygen content of the feed gas for the second stage and simultaneously reintroduce recycle methacrolein to the process again. This procedure is very sensitive to all physical parameters and stoichiometry as well as the residence time and quality of mixing with regard to safe operation. Otherwise, the higher oxygen concentration and a certain residence time within a zone comprising a higher temperature would increase the risk for a "post-combustion" effect. Post combustion is the phenomenon known for some temperature sensitive substrates such as methacrolein in form of gas mixtures which tend to decomposition into smaller fragments which might cause a spontaneous pressure increase and/or temperature rise.

3) Last but not least methacrolein cannot be completely converted in the second reaction zone. It is possible to achieve reasonable and good selectivity at conversion rates of methacrolein from 70% to 85%; at higher conversion rates, the selectivity starts to decrease significantly. In order to achieve a high yield of methacrylic acid, methacrolein must be recycled. Recycling consists of (i) quenching of process gas and (ii) absorption, desorption and optional distillation. The reintroduction of methacrolein affords the evaporation of a given recycle methacrolein quality, and it is necessary to mix evaporated crude methacrolein with oxygen containing gases such as recycle gas, air and optional steam. In some cases, an explosive gas mixture can be formed during this recycling step due to locally high temperature areas, or too high fuel concentrations above the lower explosion limit. Especially in a plant status when some equipment shows some precipitations, fouling and deposits of side products and polymeric materials, misdistribution can be observed which results, combined with too high oxygen concentrations, in critical safety conditions. Eventually this results also in an over-pressure release via safety vents or even in an explosion in some equipment parts.

A new method for increasing the process safety in an industrial scale under optimization of the yield must consider all three aspects.

For example, US 2007/0010394 describes preparation of a heteropoly acid type catalysts. Specific conditions are outlined as well as the general aspect that only partial conversion of methacrolein is achieved, resulting in a reasonable selectivity of 75% to 85%. US 2007/0010394 proposes an oxygen-methacrolein ratio in the second reaction step in a range between 2 and 2.8. Here acceptable yields are obtained. Working at the lower limit of this range, at a molar stoichiometry of 2 and under the precondition that the fuel value does not exceed 4 vol %, these parameters represent overall safe process condition, below the critical oxygen concentration. Corresponding proposals can be found in U.S. Pat. No. 6,94,362, which describes the conversion of Olefins of unsaturated aldehydes in the gas phase with a careful control of oxygen content and with recycling of Olefin. WO 2004/007405 describes computer-based control mechanism based on explosibility calculations of certain gas mixtures present in the process of methacrolein oxidation to methacrylic acid, Hammon et al.

U.S. Pat. No. 4,124,634 describes a two stages process for production of methacrylic acid, starting from isobutene. The patent addresses the most urgent safety aspect in the second stage oxidation of methacrolein to methacrylic acid, which is incomplete conversion of methacrolein in the second stage and the imperative need to limit oxygen to methacrolein mole ratio to a value below 2.0. U.S. Pat. No. 4,124,634 does not address the problem of limited catalyst lifetime under these oxygen depleted conditions, and does not provide a safe practical solution for the reintroduction of recycle methacrolein to the process.

U.S. Pat. No. 4,031,135 describes a process of propylene double partial oxidation to acrylic acid where between first and second stage oxygen depleted cooler recycling gas and air are reintroduced into the process in order to cool down the hotter first stage reaction gas.

In EP 3 007 69, MITSUI describes a special sparger design at the tie-in point of a recycle methacrolein containing gas stream and its mixing with first stage reaction gas in order to prevent post combustion effects. EP 3 007 69 describes the method of mixing the hotter first stage process gas with the colder recycle methacrolein containing gas stream. This is done by spray injection of a gas stream, optionally mixed with air, inert gas, and recirculated methacrolein by a special arrangement of spargers respectively nozzles. Caused by this injection, the hotter gas, comprising for example a temperature between 350° C. and 400° C., is cooled down to a resulting temperature between 200° C. and 240° C. Following this approach, the methacrolein containing gas mixture would contain a rich oxygen concentration of up to 13 mol % with a relatively high methacrolein concentration. As a result, an explosive gas is formed. Even if the gas mixture would be sufficiently cooled down below the ignition temperature by the spray injection, it is not possible to exclude local hot spots with the temperature above the ignition point. Hot spots are formed and observed in the sparger due to tar-like deposits and problematic polymerized residues. A critical zone for local deposits of such residues can lead to fouling and plugging of certain parts of pipes and sparger section.

In U.S. Pat. Nos. 3,876,693 and 3,147,084 the first reaction gas is cooled down by a reactor equipped with an additional heating exchanger to further cool down the reaction gas of the first reactor. The topic of safely reintroduce recycle methacrolein and oxygen is not addressed. But also, here the byproducts, especially TPA might sublimate and at least partially plug the heat exchanger tubes, reduce heat exchange efficiency and the reaction running time. In addition, the reactor architecture would be quite complex, and the manufacture and maintenance cost would be correspondingly high.

In U.S. Pat. No. 7,799,946 the recycled methacrolein is firstly passed through a quenching column where the heavy boilers including methacrylic acid are condensed. The methacrolein containing gas is absorbed and eventually desorbed and stripped from absorbed liquid to obtain gaseous mixture containing methacrolein and piped into the second reactor. Here, this gas mixture is a non-explosive gas with a sufficiently low oxygen concentration. Nevertheless, also with this approach, there would be still a risk for "post-combustion" left, especially when working at the end of the catalyst life time circle. Additionally, usage of heat exchanger cannot avoid for extended periods of operation aspects fouling and residues formation in this critical area of the process.

US 2008/021239 describes the utilization of flame arresting devices which are installed in the pipes before partial oxidation reactors to minimize the risks associated with gaseous mixture of olefins, acrolein, and methacrolein, besides certain oxygen concentration.

In conclusion, there is a considerable technical challenge in these procedures with regard to a safety-related processing. During the evaporation of the so-called recycling methacrolein, i.e. methacrolein which is not converted in the second oxidation stage, and its injection between the two oxidation reactors, one works in the so-called "lean" range very close to the explosion limit of the mixture. If this critical mixture is fed in with the process gas of the first reactor stage, e.g. at temperatures usually above 300° C., tar-like deposits and problematic compositions of the feed gas before the second oxidation reactor occur. This problem is described in a large number of documents of the state of the art and proposed solutions, which can only be counteracted by complex and expensive measures. Furthermore, the problem cannot be sufficiently compensated, especially in a continuous operation.

Here, it can be stated that so far, no process based on C4 raw material has been described in which the critical step of separating and reacting unreacted methacrolein in the process gas of the second reaction, which is usually catalyzed with a heteropolyacid, does not result in this recycle methacrolein being fed back into the second heteropolyacid-catalysed oxidation. Thus, from the state of the art, only processes are known which convert this recycle methacrolein to methacrylic acid, with all the disadvantages and technical problems described with regard to yield, catalyst life time and the safety-related implementation of the return to the second stage.

There is therefore a considerable need for improvement, especially with regard to the oxidative conversion of the recycled methacrolein in these C4-based processes.

SUMMARY OF THE INVENTION

Object

Object of the present invention was to provide a new process for the production of alkyl methacrylates, in particular of MMA, which starts from C4 building blocks and has a particularly high overall yield. At the same time, it was object of the present invention to realize a highly efficient process delivering long and extended catalyst life-time. Thereby, the process can be fully operated below critical oxygen concentrations, below critical fuel concentrations and below critical temperature conditions.

Another object of the present invention is a longer period between shutdowns, necessary for the cleaning of certain equipment parts in critical process sections, especially the sparger section, where the recycled Methacrolein with its specific impurities is reintroduced into the section between reactor 1 and 2 in gaseous form and in the presence of oxygen, water (steam) and nitrogen.

Taken all aspects together it is therefore the object of the present invention to provide a process with less shutdowns in a given period of time, longer overall productivity and safer process conditions.

Especially, it is an object of the present invention to provide a process for the manufacture of methacrylic acid respectively MMA by catalytic oxidation of isobutene in the gas phase in two spatially separate stages, in which the formation of explosive gas mixtures in the critical process sections is prohibited in a particularly simple and advantageous manner. Additionally, the inventive process allows a reduction of polymeric and high boiling compound residues in the sparger section, which otherwise leads to misdistribution of gas mixtures and critical conditions when running over longer periods without cleaning shutdowns.

Further tasks not explicitly mentioned can result from the following description of the invention without being explicitly mentioned here.

Solution

These objects have been solved by providing a novel process for the production of alkyl methacrylates and optionally methacrylic acid, especially methyl methacrylate (MMA) starting from C4 building block raw materials, especially in a process with methacrolein as intermediate.

This novel process is based on the manufacture of methacrylic acid wherein a gaseous mixture of isobutene, an oxygen containing gas, and water is reacted at least partially in a first reactor 1 to obtain a methacrolein containing process gas I. Afterwards, this process gas I is further oxidized with additional oxygen containing gas and water in a second reactor 2, whereby a process gas IV containing methacrylic acid and unconverted methacrolein is obtained.

This novel process is especially characterized in that a. The process gas I with a temperature of 300° C. to 450° C. is mixed with process gas V resulting from an evaporation section of crude methacrolein, whereby unconverted methacrolein, optionally an oxygen containing gas and water are mixed, resulting in a process gas II, b. this process gas II with a resulting temperature between 200° C. and 300° C. is mixed with a stream VI, containing another part of unconverted methacrolein, resulting in a process gas III, and c. process gas III is further oxidized in reactor 2, resulting in process gas IV.

DETAILED DESCRIPTION OF THE INVENTION

Preferably, process gas I has a temperature between 320° C. and 420° C. when exiting the first reactor. Thereby, process gas I contains less than 2000 ppm by volume Isobutene and between 2 and 6 vol % methacrolein.

In a following distillation and/or extraction step process gas IV is separated into methacrylic acid and unconverted methacrolein. The isolated recycling methacrolein is preferably stored in recycling tank. The methacrolein and organic compounds content from these two stream flows V and VI are taken from this recycling tank.

Partial flow V is formed by evaporation of recycle methacrolein and some other fuel compounds contained in it. One way to conduct the evaporation is providing the recycle methacrolein in liquid form by a pump and downstream spray this recycle methacrolein via a nozzle system onto packings which provide the necessary surface area to allow smooth evaporation. Evaporation is performed within a pressure range of 100 mbar up to 10 bars, and within a temperature range of 30° C. to 150° C. Even more preferred is the pressure range of 1 bar to 3 bar and a corresponding temperature range from 50° C. to 100° C. In this section, it is important to manage the evaporation close or above the dew point of organics mixture in order to have essentially complete evaporation of almost all present organic compounds. In this context, it is possible that partially some of the compounds with relative to methacrolein higher boiling points, such as inhibitors, methacrylic acid or terephthalic acid are not evaporated completely. These compounds might be purged together with water at one or more defined drainage points. Together with the liquid recycle methacrolein, a stream of nitrogen containing gases is passed simultaneously through the packing with co-current or counter current. The nitrogen containing gases might contain also certain amounts of oxygen, water and other inert gases, e.g. $CO_2$. Especially preferred is the utilization of recycle gas from the reaction section, which is characterized by an oxygen content below 9 vol %. Additionally, certain volumes of air can be added to the recycle gas. The gas streams are preferably preheated to a temperature between 50° C. and 150° C. in order to provide the necessary energy to evaporate the organic compounds. In an even more preferred way, steam is added in to the crude gaseous methacrolein stream for conducting the evaporation and providing sufficient amount of water in order to ensure the optimal performance of second stage catalyst. The resulting stream (see FIG. 1, stream V) in the pipe is now conveyed at a high space velocity to the sparger section directly below the exit zone of first stage reactor. By direct contact of the sparger pipe array with hot reaction gas of the first reaction zone, the gaseous recycle methacrolein stream is preheated to a temperature between 150° C. and 260° C., even more preferred to a temperature of 180° C. to 250° C. It is imperative to control the temperature of the sparger outlets in order to make sure that the local temperature does not exceed a temperature of 260° C. to 270° C. Higher temperatures might cause safety issue because temperature might be already high enough to deliver sufficient ignition energy for an uncontrolled reaction, respectively post combustion effect.

Partial flow VI is formed by liquid recycle methacrolein and it contains other fuel compounds originating from the recycled methacrolein tank via a pump. One way to reintroduce partial flow VI to the gaseous process stream II is to do the evaporation and mixing at the same time via a nozzle system which distributes the fine droplet of recycle methacrolein to the hotter process gas stream II. This task can be either solved by using a one phase nozzle system, or by using a multi-phase nozzle, respectively two-phase nozzle system. The one phase nozzle system has the advantage of simplifying the set up and recycle methacrolein in liquid form is conveyed to the nozzle and sprayed into the hot process gas stream II in form of an aerosol or droplets. Thereby, the energy is sufficient to allow smooth and residue free evaporation. Another especially preferred way to conduct the evaporation is the employment of the multi-phase respectively two-phase nozzle. As described above, the liquid mixture of crude methacrolein is conveyed and sprayed via the two-phase nozzle as one phase, whereas in one or more other phases an additional gas stream is provided in order to improve the complete and residue free evaporation. As additional gas source, the utilization of recycle gas from the reaction section is preferred. Evaporation and mixing are schematically described in mixing point 2 (MP2). Recycle gas in the current process is generated by condensing of all organic and fuel compounds from process gas stream IV. The advantage of using recycle gas or a mixture of recycle gas and additional air is the easy control of the oxygen content and temperature. It is possible as well in even another preferred way to use a nitrogen source as an additional stream in one of the nozzle phases. The additional gas stream provided in one of the nozzle phases is characterized by an oxygen content below 9 vol %, at a temperature of 0° C. to 150° C. Evaporation is performed at the pressure range of 100 mbar up to 10 bar, and in a temperature range of 200° C. to 300° C. Even more preferred is the pressure range of 1 bar to 3 bar, whereby the corresponding temperature range is from 200° C. to 270° C. Crude methacrolein from the optional recycled methacrolein tank is pumped to the nozzle at the temperature of −10° C. to 50° C. Shortly before the nozzle exit, the crude methacrolein in the pipe is heated up by the process II. Additionally, the management of the temperature of liquid recycle methacrolein before evaporation is also important to avoid recycle methacrolein polymerization and nozzle tips plugging. One way is to introduce the nitrogen containing gas in the out layer of the nozzle system and the liquid recycle methacrolein in the inner layer of the nozzle system to control the contact temperature and for reducing the heat energy. The setup of multi-phase nozzles and the presence of additional gas streams, exhibiting a cooler temperature than process gas II, effectively prohibits polymerization and fouling of the overall equipment, especially at the nozzle or the nozzle exit. After mixing with process gas II in mixing point 2, the process gas stream III will flow through the connection pipe with better mixing effect, then send into the $2^{nd}$ stage reactor for methacrolein partial oxidation reaction. The temperature of resulting process stream III obtained by mixing of the process stream II and stream VI is generally lower than the temperature of process stream II. Preferably, the maximal temperature of stream III is 1° C. to 30° C. lower than the maximum temperature of stream II. This cooling effect is advantageous and prohibits post combustion effects.

In a specific variant of the present invention, the oxygen-containing gas stream used in reactors 1 or 2 is a partially recycled gas stream resulting from the work up of process stream IV.

Recycle gas is actually organic free gas mixture with less than 1 vol % organic content, which additionally can contain carbon monoxide and carbon dioxide, besides a nitrogen content of greater than 90 vol %. Recycle gas is generated from process stream IV by condensation and absorption of almost all organic compounds with boiling points above 0° C. This resulting gas stream can be either used directly in this form to dilute oxygen rich streams, such as air, to supply oxygen depleted gas stream recycled to the certain part of the process, or it is further treated and catalytically incinerated. The recycle gas is therefore characterized by its low concentration of organic compounds, by its high concentration of nitrogen, and oxygen content between 1 vol % and 8 vol %. Instead of recycling gas, also nitrogen or mixture of nitrogen and recycle gas can be used to dilute critical process streams, respectively critical locations of the process where precise control of oxygen content is necessary, this gas mixtures can be used in a preferred variant mode of the inventive process to be introduced additionally besides liquid stream VI into the spray device. In a preferred way, this oxygen depleted gas is used as one phase in a multiphase nozzle.

In most cases partial flow VI is mixed in liquid form with process gas II. Preferably, this crude methacrolein stream VI is at least partially introduced and mixed into process gas II at a temperature below 150° C. to give the resulting process gas III. It is especially preferred to reintroduce stream VI, containing liquid methacrolein into process gas II by a spray device, especially in a mixing chamber. Also, preferably, process gas V is exiting the methacrolein evaporator section at a temperature between 30° C. and 200° C. and has a total fuel content of less than 2 vol %. In addition, process gas V might be further heated by indirectly contact with process gas I before process gas I is directly mixed with process gas V. Process gas V is further characterized by its methacrolein content of 0.5 vol % to 2 vol %, and other C2 to C5 hydrocarbons which are contained relative to methacrolein in an amount of 5 mol % to 50 mol %. The oxygen content in process gas V is higher than in process gas I and substantially higher than the oxygen content in the recycle gas but lower than the oxygen content in air.

In a preferred embodiment of the present invention, process gas IV is condensed and processed. This processing comprises preferably at least one quenching column, one crystallization step, one absorption and one desorption step in a manner to obtain a separation of crude methacrylic acid and crude methacrolein from inert gas.

It is especially preferred that the crude methacrolein of process gas V is partially reintroduced into the process as a gaseous mixture by mixing with process gas I, the evaporation of methacrolein may optionally comprise further mixing operations where additional air, inert gas and water are added.

It is very preferred to ensure that the methacrolein in process gas I contains less than 7 mol %, preferred between 0.1 mol % and 5 mol %. Other C1 to C5 saturated, including carbon monoxide, and/or unsaturated hydrocarbon compounds are present relative to methacrolein in an amount of 5 to 50 mol %, preferred between 10 and 40 mol %.

In a most preferred embodiment of the present invention the recycled liquid methacrolein and/or the crude methacrolein is stored and conveyed at a temperature below 60° C. in the presence of a stabilizer. It is even more preferred to store the crude methacrolein at the temperatures between −20° C. and 30° C.

It is a characteristic feature of the current process that process gas III has after mixing a resulting temperature between 170° C. and 300° C. The resulting temperature of process gas III after mixing of process stream VI and process stream II, optionally mixed with an inert gas, such as recycle gas and/or nitrogen, is relative to process gas II lower, especially this temperature is 1° C. to 30° C. lower.

In a specific variant of the present invention, the oxygen-containing feed gas mixtures used to perform the partial oxidations in reactors 1 or 2 may consist of a partially recycled gas stream. It is very preferred to conduct the whole process continuously.

The process according to the present invention can be used on a commercial scale, especially by converting the isolated methacrylic acid of the second reaction step by esterification with methanol to MMA in a reactor 3.

In summary, the procedure according to the present invention leads to various advantages over prior art procedures.

The advantage of the process corresponding to the present invention over the known processes is that, based on oxygen-methacrolein ratios between 1.8 and 3.2, an improved safety performance is achieved, especially at the tie-in points, where process gases are mixed with recycled methacrolein containing streams. By splitting up the recycle methacrolein volumes into a fraction to be evaporated and another fraction deemed to be sprayed and evaporated, safe conditions of resulting gas mixtures are realized. The gas injection by devices, such as a sparger, or an array of spargers, resulting from evaporation of a certain portion of the recycle methacrolein allows to cool down the first stage reaction process gas I. At this specific location, it is now possible to prevent the formation of explosive gas mixtures formed during the recycled methacrolein evaporation. It is now possible to reduce the fuel concentration of the whole gas mixture below the lower explosion limit even though the gas stream has an elevated oxygen concentration, higher than the oxygen concentration in the process gas I. The second part of recycled methacrolein was fed into the system in a liquid form through multiphase nozzles, with the temperature below 100° C. The advantages of such a set up including the multi-phase nozzle are: 1) polymerization and/or fouling in the feed line prior to the nozzle exit is prevented, 2) by forming fine droplets a better and faster evaporation and mixing with the hot process gas II can be ensured, and 3) resulting process gas III after evaporation of all liquid compounds is in an non critical condition regarding explosiveness, post combustion and post oxidation.

By mixing the methacrolein process gas II with the aerosol spray resulting from liquid recycling methacrolein stream VI, a lower temperature of process gas III at the introduction prior to reactor 2 can be ensured. This prevents a local overheating and reduces the risk of an explosion or post combustion at the critical position at or around mixing point 2. On the other hand, the process can still be conducted under optimal reaction conditions, keeping optimal performance regarding selectivity and yield, and assure a long-life time of the catalyst. Therefore, compared to known processes starting from C4 building blocks for the production of alkyl methacrylates, such as MMA, this process according to the invention leads to a high overall yield.

This results in an extended time on stream for overall process operation because downtimes and cleaning shutdowns are reduced and avoided.

Furthermore, with the process according to the invention it is possible to produce besides MMA—via a partial stream—methacrylic acid at the same time in continuous and large-scale operation in a very flexible way.

Specific Process Aspects

The process involves the isolation of recycled methacrolein and it's conditioning to adjust non-critical or relevant concentrations of methacrolein itself and process-specific by-products, such as acetone, acetaldehyde. In the following the process, especially in view of the isolation of recycle methacrolein is described briefly and as an example according to the current state of the art.

In a first tube-bundle reactor, isobutene or tert-butanol is oxidized to methacrolein at temperatures between 320° C. and over 400° C. under slight overpressure in the presence of atmospheric oxygen and water vapor, as well as recycle gas. The conversion rate is greater than 98% in the tandem process and tends to be lower in the "Separate C4 Direct Oxidation" process as both described above. Usually the residence time in the reactor with modern doped bismuth-molybdate contacts is between 1 and 10 seconds. This can be studied for example in U.S. Pat. No. 5,929,275. Gas hourly space velocity values between 1000 $h^{-1}$ and 2000 $h^{-1}$ are achieved. The exiting process gas II is mixed with the cooler, liquid recycle MAL stream VI, together with additional oxygen containing gas and optionally additional water vapour. This results in the feed gas for the second process step in reactor 2. The second oxidation stage is operated like the first one at a moderate overpressure between 0.1 bar and 2 bar and at temperatures between 260° C. and 360° C. Heteropoly acid contacts based on molybdenum and phosphorus as well as some other dopants are used for this purpose (see e.g. US 2007/0010394). The modified heteropoly acids still show a high dependence on selectivity and conversion. This applies in so far as higher conversion rates tend to result in significantly lower selectivity. For this reason, the conversion and the associated catalyst loading is adjusted between 65% and 85%. For all processes and their modifications, it is therefore necessary to separate unreacted methacrolein from the process gas IV respectively from the desired product methacrylic acid and to return it directly or indirectly to the second oxidation reactor as so-called recycle methacrolein. As for the present invention, the recycling methacrolein is returned indirectly as described above.

The methacrolein-containing mixture separated from the methacrylic acid after the second reaction stage, referred to as recycled methacrolein according to the invention, contains, depending on the catalyst quality and parameters of the process performance, other by-products in addition to methacrolein. Following the state of the art, the following range of by-products for the recycling methacrolein after separation from the crude methacrylic acid can be expected as an example:

| 0.5-4 | wt % | Acetaldehyde |
| 1-8 | wt % | Acetone |
| 1-5 | wt % | Acrolein |

-continued

| 0.05-0.4 | wt % | Butan-2,3-dion |
| 0.2-1.5 | wt % | MMA |
| 1-5 | wt % | Water |
| 1-5 | wt % | Methacrylic acid |
| 0.1-3 | wt % | Acetic acid |
| 70-95 | wt % | Methacrolein |

Depending on the process used (tandem or intermediate isolation of methacrolein), a methacrolein content of more than 70 wt % is characteristic of recycling MAL. Furthermore, the recycling contains both lower-boiling components such as acetone, acrolein and acetaldehyde and higher-boiling components such as MMA, water and methacrylic acid.

The hot process gas IV usually leaves reactor 2 at 250° C. to 360° C. and must first be cooled. Usually, it is first cooled down to a temperature between 150° C. and 250° C. using a recuperative heat exchanger. Recuperative heat exchanger is preferred because they use the heat to generate steam. Afterwards, the gas phase, which is now reduced in temperature, is usually passed into a circulating condensed quench phase at temperatures between 50° C. and 100° C. This quench phase can be the sump section of a quench column, which is circulated and thermostatic by a pump. At the head of this quench column, most of the methacrolein passes in gaseous form together with the process gas, while most of the methacrylic acid formed is condensed and quenched in the sump. In the next process step methacrolein is condensed or absorbed together with water. In this step, the recycled methacrolein is produced in liquid form together with all condensable secondary components, such as low boilers. Nevertheless, an effective separation from the process gas, which escapes at the head of this column, is achieved. In a final step, methacrolein is now desorbed from the absorber phase and the recycling methacrolein is obtained, which has a purity of more than 70% by weight. A crude recycle methacrolein is produced in this way, which can now be piped into a recycling tank. Surprisingly, it was found that also the by-products in the recycling methacrolein, especially reactive low boilers such as acrolein and acetaldehyde as well as other components, are converted without substantial effects on the selectivity of the main reaction or on the catalyst performance in general in such a way that the by-products of the side reaction can be effectively separated from the desired MMA respectively methacrylic acid.

Figure 1:
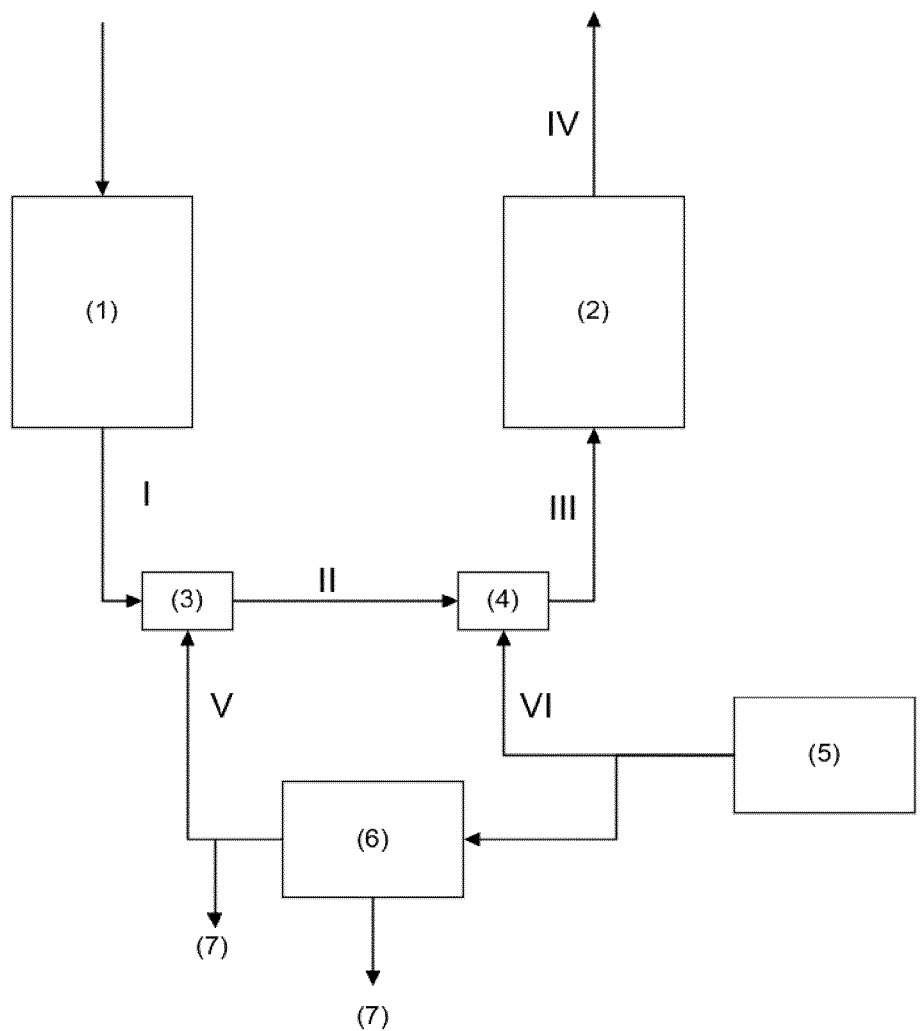
FIG. 1 shows one embodiment of the inventive process flow, which contains main process streams and major equipment parts.

(1) Reactor 1: contains first catalyst, salt bath reactor, performance the first stage oxidation from isobutene to methacrolein.

(2) Reactor 2: contains second catalyst, salt bath reactor, performance the second stage oxidation from methacrolein to methacrylic acid (3) Mixing Point 1

Process gas reaction stage 1, consisting mainly of methacrolein, methacrylic acid and acetic acid, besides CO and $CO_2$, exits the reactor tubes with the temperature of 320° C. to 420° C., oxygen content below 5 vol %. This gas heats up the incoming recycle methacrolein gas stream. Mixing Point 1 is a typically array of pipes and sparger—nozzle combinations.

(4) Mixing Point 2 is a mixing device or section in the process where process gas II is mixed with process stream VI. Mixing gas after mixing point 1, consisting mainly of methacrolein, recycled methacrolein, methacrylic acid and acetic acid, besides CO and $CO_2$, with a temperature of 200° C. to 300° C. and an oxygen content below 10 vol %. This gas heats up and evaporates a part of the incoming recycle methacrolein stream which is provided as an aerosol from process stream VI. Mixing Point 2 is typically an array of pipes and sparger—nozzle combinations.

(5) Recycle methacrolein tank: short time storage, optional cooling, and intermediate buffer, upstream mixing point 1 and 2.

(6) Recycle methacrolein evaporator (7) Drainage

Optionally one or more drainage points either directly in the recycle methacrolein evaporator section, or in the pipe sending gaseous mixture to the mixing point 1. Here discontinuously or continuously water or high boiler fraction are removed from the equipment in order to control physical fouling and residues. Residues may contain terephthalic acid, or similar compounds as well as radical inhibitors and part of methacrylic acid.

Process Stream I:

Process gas reaction stage 1, consisting mainly of methacrolein, methacrylic acid and acetic acid, besides CO and $CO_2$, exits the reactor tubes with the temperature of 320° C. to 420° C. and an oxygen content below 5 vol %.

Process Stream II:

Mixing gas from mixing point 1, consisting mainly of methacrolein, methacrylic acid and acetic acid, besides CO and $CO_2$, with the temperature of 200° C. to 300° C. and an oxygen content below 10 vol %.

Process Stream III:

Mixing gas from mixing point 2, consisting mainly of methacrolein, methacrylic acid and acetic acid, besides CO and $CO_2$, with the temperature of 200° C. to 300° C. and an oxygen content below 10 vol %.

Process Stream IV:

Process gas reaction stage 2, consisting mainly of methacrylic acid, unreacted methacrolein, and acetic acid, besides CO and $CO_2$, exits the reactor tubes with the temperature of 250° C. to 350° C., oxygen content below 8 vol %.

Process stream V:

Gaseous nitrogen containing stream contains evaporated methacrolein with all volatile organic compounds as well as water (as steam) and oxygen.

Process stream VI:

Liquid phase contains unreacted methacrolein with all other isolated organic compounds under the temperature range of −20° C. to 20° C. before mixing point 2. Shortly before mixing point 2, the part of pipe is in contact with process stream II, therefore heating liquified methacrolein before the nozzle exit to the temperature below 150° C.

EXAMPLES

Example 1

A feed gas containing isobutylene as a raw material and oxygen, water at a molar ratio of 1:2:1.5 was fed to the $1^{st}$ reactor, which temperature was controlled at 350° C. with a reactor inlet pressure 1.2 bar gauge, to give an hourly space velocity of 1,000 $hr^{-1}$, whereby the reaction was conducted in a shell-and-tube reactor with a catalyst of oxides of molybdenum components, which was produced based on US 2007/0010394. Afterwards, the resulted process gas I with a temperature of 343° C., which was comprising as following: 4.8 vol % methacrolein, 0.74 mol % of CO, 0.21 mol % of methacrylic acid, 0.21 mol % of acetic acid, 0.12 mol % of acetone, 0.21 mol % of acetaldehyde, 0.04 mol % of acrolein, 0.03 mol % of formaldehyde, 0.03 mol % of acrylic acid, 250 ppm of isobutene and 3.5 vol % of oxygen, was obtained. The isobutylene conversion is 99.6%, and methacrolein yield was 79.6%. Then a process gas V which the partly recycled methacrolein after evaporation, at a temperature of 80° C. which was comprising as following: 1.41 mol % of fuel that containing 1.2 mol % of methacrolein, 0.03 mol % methacrylic acid, 0.09 mol % acetone, 0.05 mol % acetaldehyde, 0.04 mol % acrolein, 17 mol % of oxygen and 13 mol % of water were mixed with process gas I by the volume flowrate ratio of 1:0.8, resulting process gas II with a temperature of 245° C. The crude methacrolein containing 85 wt % methacrolein, 2.5 wt % methacrylic acid, 4.5 wt % acetone, 3.5 wt % acetaldehyde, 3 wt % acrolein, 1 wt % water, 200 ppm inhibitor, with a gas containing 7.5 mol % oxygen injected to the process gas II by a two-phase nozzle at a temperature 50° C. The resulted process gas III had a molar ratio of 1:2.73:4.1 from methacrolein, oxygen and water, and total contained 4.48 mol % of fuel, which was composing 3.44 mol % of methacrolein and 0.41 mol % of CO, 0.12 mol % of methacrylic acid, 0.12 mol % of acetic acid, 0.15 mol % of acetone, 0.15 mol % of acetaldehyde, 0.06 mol % of acrolein, 0.02 mol % of formaldehyde and 0.01 mol % of acrylic acid. Then process gas III was passed through $2^{nd}$ reactor which was filled with a catalyst of a mixture of phosphomolybdate which was produced based on US 2007/0010394, conducted the reaction at the 300° C. with an hourly space velocity of 1,000 $h^{-1}$. The conversion of methacrolein was 80%. The process flow is shown in FIG. 1.

The results showed that process gas I and IV gaseous components did not form explosive gases because oxygen concentration was highly diluted. Process gas II and III gaseous components formed relevantly higher oxygen concentration to reach 2.73 of the $O_2/MAL$, but non-explosive gases because the combustible fuel concentration which was composing methacrolein, all organics and CO, was higher than upper explosion limit. Process gas V gaseous components also did not form an explosive gas, because the combustible fuel concentration was lower than lower explosion limit.

Figure 2:
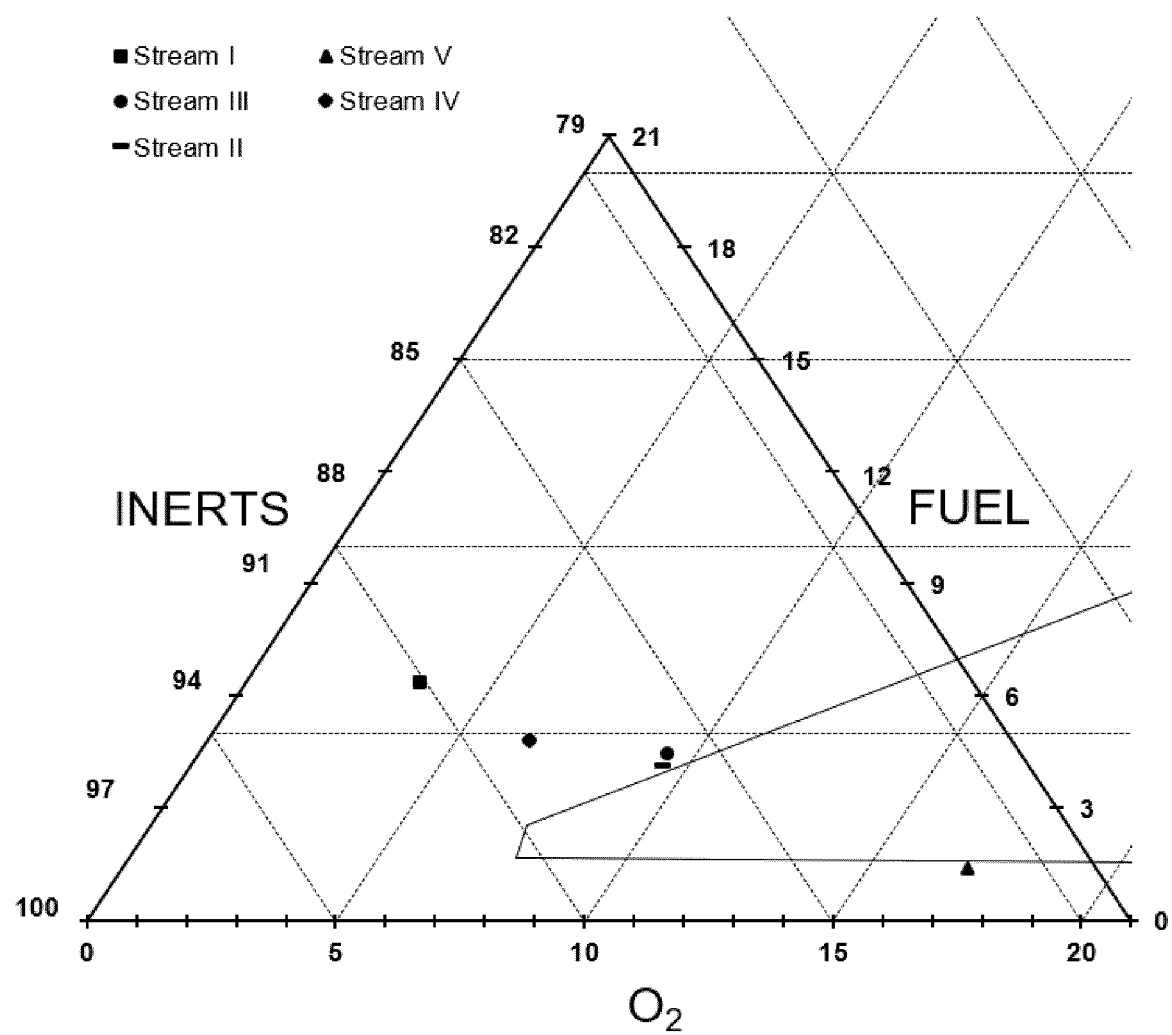
FIG. 2 shows the position of the different operation streams in the flammability diagram of example 1.

The components of results are shown in Table 1, the process gas stream operating points are shown in the FIG. 2 with explosion zone.

TABLE 1

| Process gas | MAL | $O_2$ | $H_2O$ | C1-C5 | CO | Fuel | Critical $O_2$ conc. | Critical fuel to $O_2$ value | Critical post combustion |
|---|---|---|---|---|---|---|---|---|---|
| I | 4.8 | 3.5 | 14.6 | 0.85 | 0.74 | 6.39 | NO | >UEL | NO |
| II | 3.27 | 9.5 | 13.4 | 0.59 | 0.41 | 4.27 | YES | >UEL | NO |
| III | 3.44 | 9.4 | 14 | 0.63 | 0.41 | 4.48 | YES | >UEL | NO |
| IV | 0.7 | 6.5 | 15 | 3.13 | 1 | 4.83 | NO | >UEL | NO |
| V | 1.2 | 17 | 13 | 0.21 | — | 1.41 | YES | <LEL | NO |

All contents listed in mol %
Fuel = MAL + CO + C1~C5

The process conditions and parameters according to example 1 where kept for an uninterrupted continuous period of 2100 hours and the gas compositions were checked on a regular basis. Analysis confirmed that no significant changes in the gas compositions as well as of the temperature and pressures were observed. After physical inspection of the critical equipment parts, such as piping, evaporator section including packings or sparger section, no major deposits were observed. As a result of this analysis and observation, it is confirmed that the catalyst is in an optimal performance condition. During this time on stream period, no pressure or temperature increase in anyone of the critical gas compositions could be detected, demonstrating that critical post combustion conditions were effectively prevented.

Example 2

A reaction was conducted in the same manner as in Example 1 except that the molar ratio of 1:2.5 from methacrolein and oxygen to the reactor 2 is lower than Example 1 by adjusting air and recycle gas ratio. In this Example 2, the process gas V which the partly recycled methacrolein after evaporation, at a temperature of 80° C. which was comprising as following: 1.44 mol % of fuel that containing 1.21 mol % of methacrolein, 0.03 mol % methacrylic acid, 0.10 mol % acetone, 0.05 mol % acetaldehyde, 0.05 mol % acrolein, 16.7 mol % of oxygen and 13 mol % of water were mixed with process gas I, resulting process gas II with a temperature of 245° C. The crude methacrolein containing 85 wt % methacrolein, 2.5 wt % methacrylic acid, 4.5 wt % acetone, 3.5 wt % acetaldehyde, 3 wt % acrolein, 1 wt % water, 200 ppm inhibitor, with a gas containing 6.5 mol % oxygen injected to the process gas II by a two-phase nozzle at a temperature 50° C. The resulted process gas III had a molar ratio of 1:2.5:4.1 from methacrolein, oxygen and water, and total contained 4.38 mol % of fuel, which was composing 3.34 mol % of methacrolein and 0.41 mol % of CO, 0.12 mol % of methacrylic acid, 0.12 mol % of acetic acid, 0.15 mol % of acetone, 0.15 mol % of acetaldehyde, 0.06 mol % of acrolein, 0.02 mol % of formaldehyde and 0.01 mol % of acrylic acid. Then process gas III was passed through reactor 2 which was filled with a catalyst of a mixture of phosphomolybdate which was produced based on US 2007/0010394, conducted the reaction at the 300° C. with an hourly space velocity of 1,000 h$^{-1}$. The conversion of methacrolein was 80%. The process flow is shown in FIG. 1.

The results showed that, process gas I and IV gaseous components did not form explosive gases because oxygen concentration was highly diluted. Process gas II and III gaseous components formed lower oxygen concentration compared to Example 1 to reach 2.5 of the $O_2$/MAL, non-explosive gases because the combustible fuel concentration which was composing methacrolein, all organics and CO, was higher than upper explosion limit and also non critical oxygen concentration generated. Process gas V gaseous components also did not form an explosive gas, because the combustible fuel concentration was lower than lower explosion limit.

Figure 3:
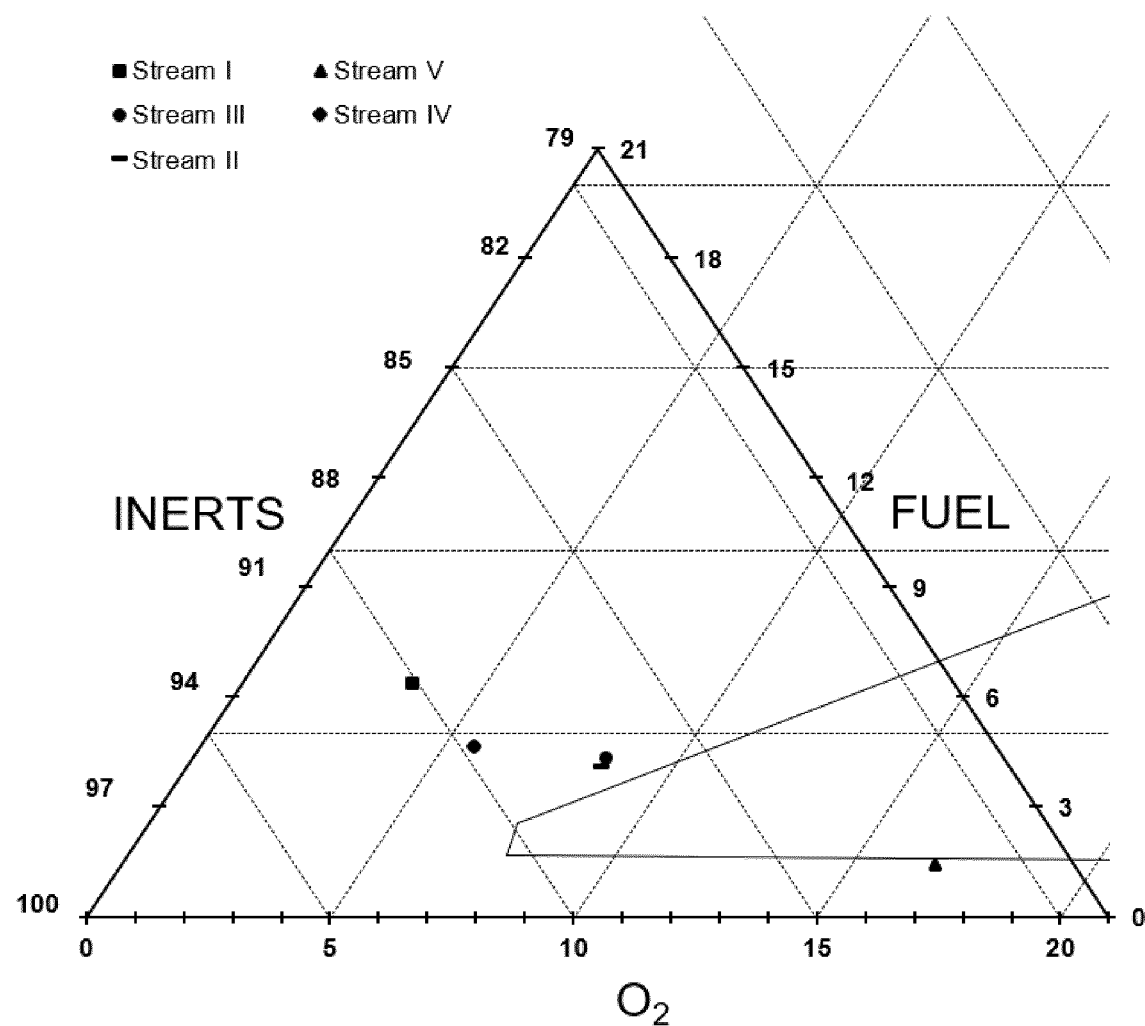
FIG. 3 shows the position of the different operation streams in the flammability diagram of example 2.

The components of results are shown in Table 2, the process gas stream operating points are shown in the FIG. 3 with explosion zone.

TABLE 2

| Process gas | MAL | $O_2$ | $H_2O$ | C1-C5 | CO | Fuel | Critical $O_2$ conc. | Critical fuel to $O_2$ value |
|---|---|---|---|---|---|---|---|---|
| I | 4.8 | 3.5 | 14.6 | 0.85 | 0.74 | 6.39 | NO | >UEL |
| II | 3.18 | 8.5 | 13.4 | 0.59 | 0.41 | 4.18 | NO | >UEL |
| III | 3.34 | 8.45 | 14 | 0.63 | 0.41 | 4.38 | NO | >UEL |
| IV | 0.67 | 5.64 | 15 | 3.09 | 0.9 | 4.66 | NO | >UEL |
| V | 1.21 | 16.7 | 13 | 0.23 | — | 1.44 | YES | <LEL |

All contents listed in mol %
Fuel = MAL + CO + C1~C5

The process conditions and parameters according to example 2 where kept for an uninterrupted continuous period of 2100 hours and the gas compositions were checked on a regular basis. Analysis confirmed that no significant changes in the gas compositions as well as of the temperature and pressures were observed. After physical inspection of the critical equipment parts, such as piping, evaporator section including packings or sparger section, no major deposits were observed. As a result of this analysis and observation, it is confirmed that the catalyst is in an optimal performance condition.

Comparative Example

Figure 4:
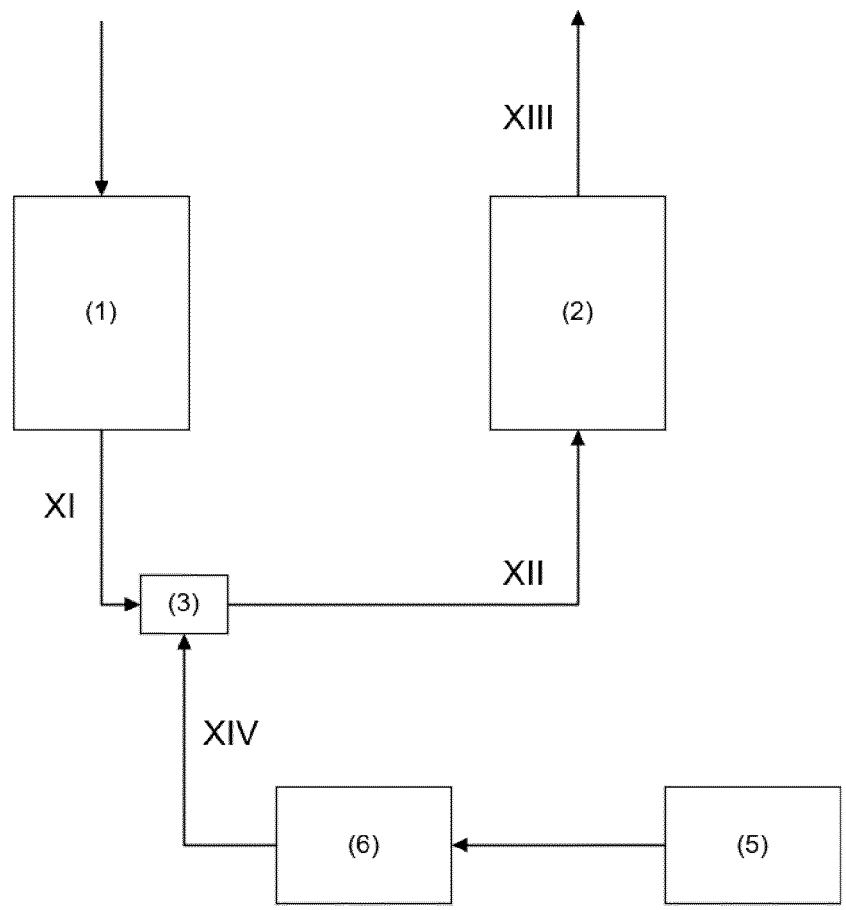
FIG. 4 shows the comparative example process flows.

A reaction was conducted in the same manner as in Example 1 except that all recycled methacrolein is introduced into process gas I by the methacrolein evaporator, resulting in a new process gas XIV which is comprising as following: 1.74 mol % of methacrolein, 0.05 mol % of methacrylic acid, 0.09 mol % of acetone, 0.07 mol % of acetaldehyde, 0.06 mol % of acrolein, 16.7 mol % of oxygen and 13.5 mol % of water with 80° C., mixed with process gas XI which is the same as process gas I, resulting process gas XII at 240° C., which has a methacrolein, oxygen and water ratio of 1/2.79/4.1, and total contains 4.44 mol % of fuel, which is comprising as following: 3.41 mol % of methacrolein and 0.40 mol % of CO, 0.12 mol % of methacrylic acid, 0.12 mol % of acetic acid, 0.15 mol % of acetone, 0.15 mol % of acetaldehyde, 0.06 mol % of acrolein, 0.02 mol % of formaldehyde and 0.01 mol % of acrylic acid. The conversion of methacrolein was also 80%. The process flow is shown in FIG. 4.

The results showed that, process gas XI and XIII gaseous components did not form explosive gases because oxygen concentration was highly diluted. Process gas XII gaseous composition formed relevantly higher oxygen concentration to reach 2.79 of the $O_2$/MAL, but a non-explosive gas because the combustible fuel concentration which was containing methacrolein, all organics and CO, was higher than upper explosion limit. However, process gas XIV gaseous components formed an explosive gas, besides higher oxygen concentration, the combustible fuel concentration was higher than example 1 and reached lower explosion limit.

Figure 5:
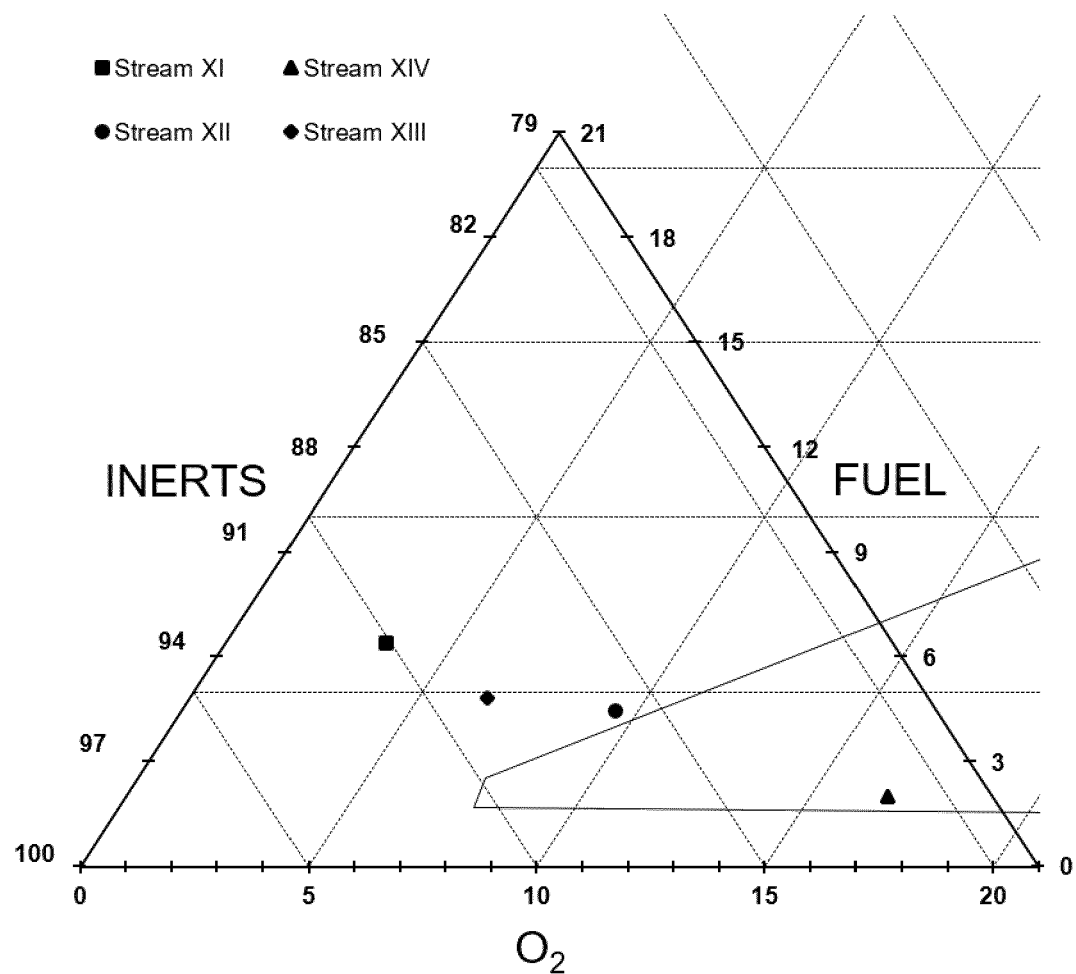
FIG. 5 shows the position of the different operation streams in the flammability diagram of the comparative example.

The components of results are shown in Table 3, the process gas stream operating points are shown in the FIG. 5 with explosion zone.

TABLE 3

| Process gas | MAL | $O_2$ | $H_2O$ | C1-C5 | CO | Fuel | Critical $O_2$ conc. | Critical fuel to $O_2$ value |
|---|---|---|---|---|---|---|---|---|
| XI | 4.8 | 3.5 | 14.6 | 0.85 | 0.74 | 6.39 | NO | >UEL |
| XII | 3.41 | 9.5 | 14.0 | 0.63 | 0.4 | 4.44 | YES | >UEL |
| XIII | 0.7 | 6.5 | 15 | 3.13 | 1 | 4.83 | NO | >UEL |
| XIV | 1.74 | 16.7 | 13.5 | 0.27 | — | 2.01 | YES | >LEL |

All contents listed in mol %
Fuel = MAL + CO + C1~C5

The process conditions and parameters according to the comparative example where kept for an uninterrupted continuous period of 2100 hours and the gas compositions were checked on a regular basis. Analysis confirmed that no significant changes in the gas compositions as well as of the temperature and pressures were observed. After physical inspection of the critical equipment parts, such as piping, evaporator section including packings or sparger section, some deposits in sparger section and the connection pipe between evaporator and sparger were observed.

The invention claimed is:

1. A process for the manufacture of methacrylic acid, the process comprising:
   reacting in a first reactor a gaseous mixture of isobutene, an oxygen containing gas, and water, to obtain a methacrolein containing process gas I, and
   further oxidizing process gas I with additional oxygen containing gas and water in a second reactor, to obtain a process gas IV containing methacrylic acid and unconverted methacrolein,
   wherein
   process gas I with a temperature of 300° C. to 450° C. is mixed with a process gas V resulting from an evaporation section of crude methacrolein, whereby unconverted methacrolein, an oxygen containing gas and water are mixed, resulting in a process gas II,
   process gas II with a resulting temperature between 200° C. and 300° C. is mixed with a stream VI, containing another part of unconverted methacrolein, resulting in a process gas III, and
   process gas III is further oxidized in a second reactor, resulting in process gas IV.

2. The process according to claim 1, wherein process gas I, when exiting the first reactor with a temperature between 320° C. and 400° C., contains less than 2000 ppm by volume of isobutene and between 2 and 6 vol % of methacrolein.

3. The process according to claim 1, wherein process gas V is exiting the evaporation section at a temperature between 30° C. and 200° C., and has a total fuel content of less than 2 vol %, and
   wherein process gas V is further healed, optionally by indirect contact with process gas I, before process gas I is directly mixed with process gas V.

4. The process according to claim 1, wherein
   process gas IV is condensed and processed, whereby processing comprises at least one quenching column, one crystallization step, and one absorption and desorption step in a manner to obtain a separation of crude methacrylic acid and crude methacrolein from inert gas, and
   the crude methacrolein is partially introduced and mixed into process gas II at a temperature below 100° C. to give process gas III.

5. The process according to claim 1, wherein the crude methacrolein of process gas V is partially reintroduced into the process as a gaseous mixture, by mixing with process gas I after mixing with additional air, inert gas and water, and the other part of recycling methacrolein in stream VI is reintroduced into the process in liquid form by a spray device.

6. The process according to claim 1, wherein process gas I contains less than 7 wt. % of $C_1$-$C_5$ saturated and unsaturated hydrocarbon compounds unlike the methacrolein, and at least 65 wt. % of the methacrolein.

7. The process according to claim 3, wherein a crude methacrolein stream is partially conveyed in liquid form and inserted into process gas II by a spray device and an additional gaseous stream containing nitrogen is mixed into process gas II.

8. The process according to claim 1, wherein recycled liquid methacrolein and/or the crude methacrolein is stored and conveyed at a temperature below 60° C. in the presence of a stabilizer.

9. The process according to claim 1, wherein process gas III has a temperature between 150° C. and 300° C. after mixing process gas II and stream VI.

10. The process according to claim 6, wherein process gas I contains between 0.1 and 5 wt. % of the $C_1$-$C_5$ saturated and unsaturated hydrocarbon compounds, and between 75 and 99.9 wt. % of the methacrolein.

* * * * *